(12) United States Patent
Dukor et al.

(10) Patent No.: US 6,274,871 B1
(45) Date of Patent: Aug. 14, 2001

(54) METHOD AND SYSTEM FOR PERFORMING INFRARED STUDY ON A BIOLOGICAL SAMPLE

(75) Inventors: Rina K. Dukor, Elmhurst, IL (US); Curtis A. Marcott, Cincinnati, OH (US)

(73) Assignees: VYSIS, Inc., Downers Grove, IL (US); The Procter and Gamble Company, Cincinnati, OH (US)

(*) Notice: Subject to any disclaimer, the term of this patent is extended or adjusted under 35 U.S.C. 154(b) by 0 days.

(21) Appl. No.: 09/176,792

(22) Filed: Oct. 22, 1998

(51) Int. Cl.[7] .............................. G01B 9/02; G01N 21/35

(52) U.S. Cl. ................................... 250/339.8; 250/339.2; 250/339.12

(58) Field of Search .............................. 250/339.8, 339.2, 250/339.12

(56) References Cited

U.S. PATENT DOCUMENTS

| | | | |
|---|---|---|---|
| 5,153,675 | * | 10/1992 | Beauchaine ............... 250/339.08 |
| 5,160,826 | * | 11/1992 | Cohen et al. ............. 250/339.08 |
| 5,528,368 | * | 6/1996 | Lewis et al. .............. 250/339.02 |

* cited by examiner

*Primary Examiner*—Constanine Hannaher
*Assistant Examiner*—Otilia Gabor
(74) *Attorney, Agent, or Firm*—Leydig, Voit & Mayer, Ltd.

(57) ABSTRACT

A method and system performs Fourier transform infrared (FT-IR) imaging microspectroscopy on a biological sample fixed on a substrate with a supporting surface that generally reflects infrared light while generally transmitting visible light. Infrared light impinging on the biological sample is reflected by the supporting surface of the substrate. Infrared light from the sample is focused onto a focal-plane array detector with multiple pixels for detecting infrared images of the sample. The detected infrared images are processed to generate spectral images of the sample. The same biological sample is suitable for conventional pathological studies.

29 Claims, 4 Drawing Sheets

METHOD AND SYSTEM FOR PERFORMING INFRARED STUDY ON A BIOLOGICAL SAMPLE

FIELD OF THE INVENTION

This invention relates generally to the examination of biological samples for identifying cellular types or the presence of cellular anomalies. More particularly, the invention relates to the use of infrared microspectroscopy to study biological samples for identifying cellular types or the presence of anomalies.

BACKGROUND OF THE INVENTION

In the past decade, applications of spectroscopy and microspectroscopy have greatly advanced into areas of clinical study. The potential of various spectroscopic techniques for screening and disease diagnosis in clinical settings has been investigated.

For instance, infrared microspectroscopy has been used in the study of biological samples. As is well known, this technique involves illuminating the sample being studied with infrared light, and collecting the infrared light from a selected microscopic region of the sample to derive the absorption spectrum of that region. The measured infrared spectra from different regions of the sample are analyzed to identify cell types or anomalies. The results of the spectroscopic measurements are typically compared to the results of a study by a pathologist on a separate sample from the same source for classification.

Recently, Fourier Transform Infrared (FT-IR) spectroscopic imaging microscopy has been developed into a very powerful analytical technique. This technique uses a focal-plane array detector attached to an FT-IR microscope to collect infrared images of an area of interest on the sample. The focal-plane array detector includes an array (e.g., 64×64) of pixels, each capable of independently detecting the intensity of infrared light impinging thereupon. A significant advantage of this technique as compared to more conventional infrared microspectroscopy is the parallel infrared detection of a relatively large number of pixels, which eliminates the need of point-by-point mapping of the sample. This parallel detection significantly reduces the time required to collect infrared spectra of a given sample.

The FT-IR imaging microscopy, however, is not readily applicable to biological samples conventionally prepared for pathological studies. The FT-IR imaging microspectroscopy is typically performed in a transmission mode. For that purpose, the sample is fixed on a window made of an infrared-transparent material, such as $BaF_2$ or $CaF_2$. Infrared light for illuminating the sample is directed through the window to the sample, and the infrared light passed through the sample is collected for spectral analysis. In contrast, a pathologist uses visible microscopy to analyze a biological sample. A biological sample for pathological studies is typically a thin section fixed on a glass slide and stained. Glass slides, which are transparent to visible light, are strongly absorptive in the mid-infrared range that is important for spectral analysis. As a result, a biological sample prepared for conventional pathological studies cannot be used for FT-IR imaging.

It is possible to mount a biological sample on an infrared-transparent window so that it can be studied with FT-IR spectroscopy. This approach is not preferred, however, for several reasons. The infrared-transparent window, which is typically made of a certain type of salt, may react with the biological sample supported thereon. Moreover, infrared-transparent windows are very expensive and more difficult to handle than conventional glass slides. Furthermore, perhaps the most significant drawback of this approach is that the sample prepared for the infrared study is damaged in the sense that it cannot later be recovered for examination by a pathologist to verify the diagnoses based on the infrared measurements or to perform any other pathologic studies. The use of different samples prepared in different ways, albeit from the same source, for infrared spectroscopic and conventional pathological studies inevitably introduces some unreliability in the comparison of the results of the two studies.

SUMMARY OF THE INVENTION

In view of the foregoing, it is a primary object of the invention to provide a method and system for performing FT-IR imaging microspectroscopy on a biological sample that allows the same biological sample to be used for conventional pathological studies.

It is a related and more specific object of the invention to study a biological sample with both the FT-IR imaging microspectroscopy and the conventional pathological studies by preparing the biological sample in such a way that is suitable for both FT-IR imaging and pathological studies.

It is a further related object of the invention to provide a way to prepare a biological sample suitable for both FT-IR imaging and conventional pathological studies that is simple and relatively inexpensive.

In accordance with these and other objects of the invention, there is provided a method and system for identifying cellular types and/or anomalies in a biological sample with FT-IR imaging microspectroscopy that allows the same sample to be examined with conventional pathological studies. The biological sample is fixed on a substrate that has a supporting surface that is generally transparent to visible light and generally reflective to infrared light. The transparency of the supporting surface for visible light facilitates pathological studies of the biological sample based on visual examination. The reflectivity of the supporting surface for infrared light enables infrared analysis of the sample using the FT-IR imaging microspectroscopy technique. To perform the FT-IR imaging, an area of interest on the biological sample is selected by visual inspection and positioned for FT-IR imaging in a reflection mode. Infrared light is directed to impinge on the sample for illumination thereof. The infrared light reflected by the infrared-reflective supporting surface and through the sample is focused on a focal-plane array detector with multiple pixels. The infrared images of the area of interest collected by the array detector are used to derive an infrared spectrum for each pixel of the array detector. Pathological studies performed on the same biological sample can be compared to the results of the infrared spectroscopic study.

The term "cellular type" is meant to include any of a number of states which are said to characterize cells such as benign, hyperplastic, and malignant, and different types of cells such as epithelial cells (found in lobules, ducts and elsewhere), endothelial cells (found in blood vessels and elsewhere), and fibroblasts (found in connective tissue and elsewhere), and others. Abnormal cells, such as cancerous cells, are considered anomalous and are identifiable by the method of the invention. Thus, the method of the invention is useful in cancer diagnostics and for monitoring changes in cellular types as related to disease state over time.

Other objects and advantages will become apparent with reference to the following detailed description when taken in conjunction with the drawings.

Figure 1:
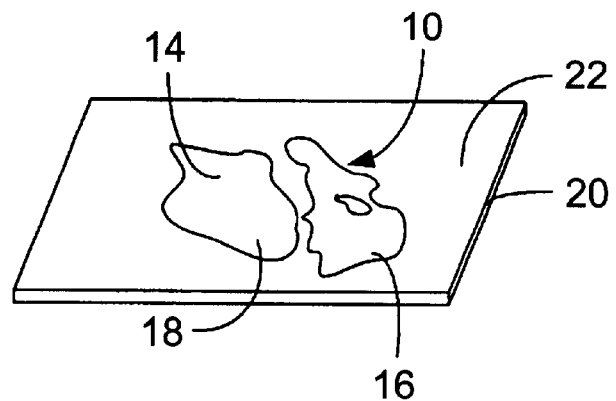
FIG. 1 is a schematic top view of a biological sample that may be studied using the method and system of the invention.

While the invention is susceptible to various modifications and alternative constructions, certain illustrated embodiments have been shown in the drawings and will be described below. It should be understood, however, that there is no intention to limit the invention to the specific forms disclosed, but, on the contrary, the invention is to cover all modifications, alternative constructions and equivalents falling within the spirit and scope of the invention as defined by the appended claims.

DETAILED DESCRIPTION OF THE PREFERRED EMBODIMENT

Turning now to the drawings, FIG. 1 shows, in schematic form, a biological sample 10 which can be studied by the method of the invention. The biological sample 10 is in the form of a thin layer supported on a substrate. The biological sample 10 contains cells of different cellular types, which can be identified using the method of the invention. For instance, the sample 10 may contain benign, hyperplastic, and malignant cells at different sites 14, 16, 18, respectively.

In accordance with an important aspect of the invention, the substrate 20 supporting the sample 10 has a supporting surface 22 that is generally transparent to visible light but generally reflective to infrared light. As will be described in greater detail below, a significant advantage of the invention is that the same biological sample can be studied for both FT-IR imaging microscopy and conventional pathological studies. More particularly, the reflectivity of the supporting surface 22 in the infrared range enables the biological sample 10 to be studied by the FT-IR imaging microspectroscopy technique in the reflective mode. On the other hand, due to the transparency of the supporting surface 22, the substrate behaves like a conventional glass slide in the visible range. As a result, pathological studies can be performed on the same biological sample.

Another significant advantage of the invention is that such a substrate with the specified optical properties is readily available and costs significantly less than conventional infrared-transmitting windows used in infrared transmission studies. For example, U.S. Pat. No. 5,160,826, which is hereby incorporated by reference, describes a window having a coating that generally transmits visible radiation while generally reflecting radiation across the infrared range. This coating includes a mono-atom layer of silver that is typically 85% to 95% reflective of infrared radiation while transmitting most visible light. The silver layer is coated with a protective layer that is transparent to most radiation across the visible and infrared ranges. Windows of such construction are commercially available from, for example, Kevley Technologies, Inc. in Chesterland, Ohio.

Figure 2:
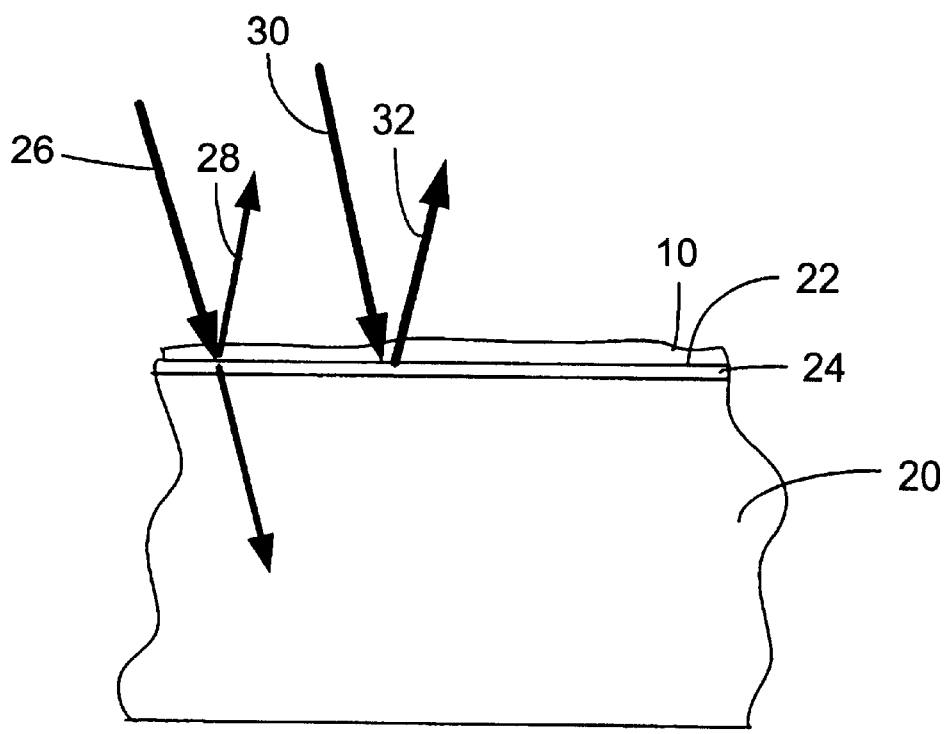
FIG. 2 is a schematic cross sectional view of the biological sample supported on a substrate with a supporting surface that is generally transparent to visible light and generally reflective to infrared light.

With the infrared-reflective supporting surface, the biological sample is suitable for study with the FT-IR imaging microspectroscopy technique operated in a reflection mode. FIG. 2 shows an enlarged cross sectional view of the biological sample 10 mounted on the substrate 20. In the illustrated embodiment, the supporting surface 22 of the substrate includes a generally infrared-reflective and visible-transmitting coating 24. Incident infrared light 30 impinging on the biological sample 10 passes through the sample and is reflected by the infrared-reflective supporting surface 22, and the reflected infrared light passes again through the sample. The infrared light 32 leaving the sample can be collected for analyzing the infrared absorption spectroscopic information of the sample.

On the other hand, the transmission of visible light by the coating 24 also allows the sample to be studied with visible light. As illustrated in FIG. 2, the sample 10 can be illuminated in a transmission mode by passing the illuminating visible light 36 through the substrate 20 and the coating 24 into the sample. Visible light 38 transmitted through or scattered by the sample may then be collected by an objective of a microscope for viewing or imaging. This transmission mode of visible illumination is commonly used by pathologists in studying biological samples. Alternatively, the sample may be illuminated with visible light in the reflection mode. As illustrated in FIG. 2, visible light 26 impinging on the sample 10 is partially reflected by the sample, and the remaining visible light is generally transmitted through the substrate 20. The visible light 28 reflected by the sample may then be collected for viewing.

Figure 3:
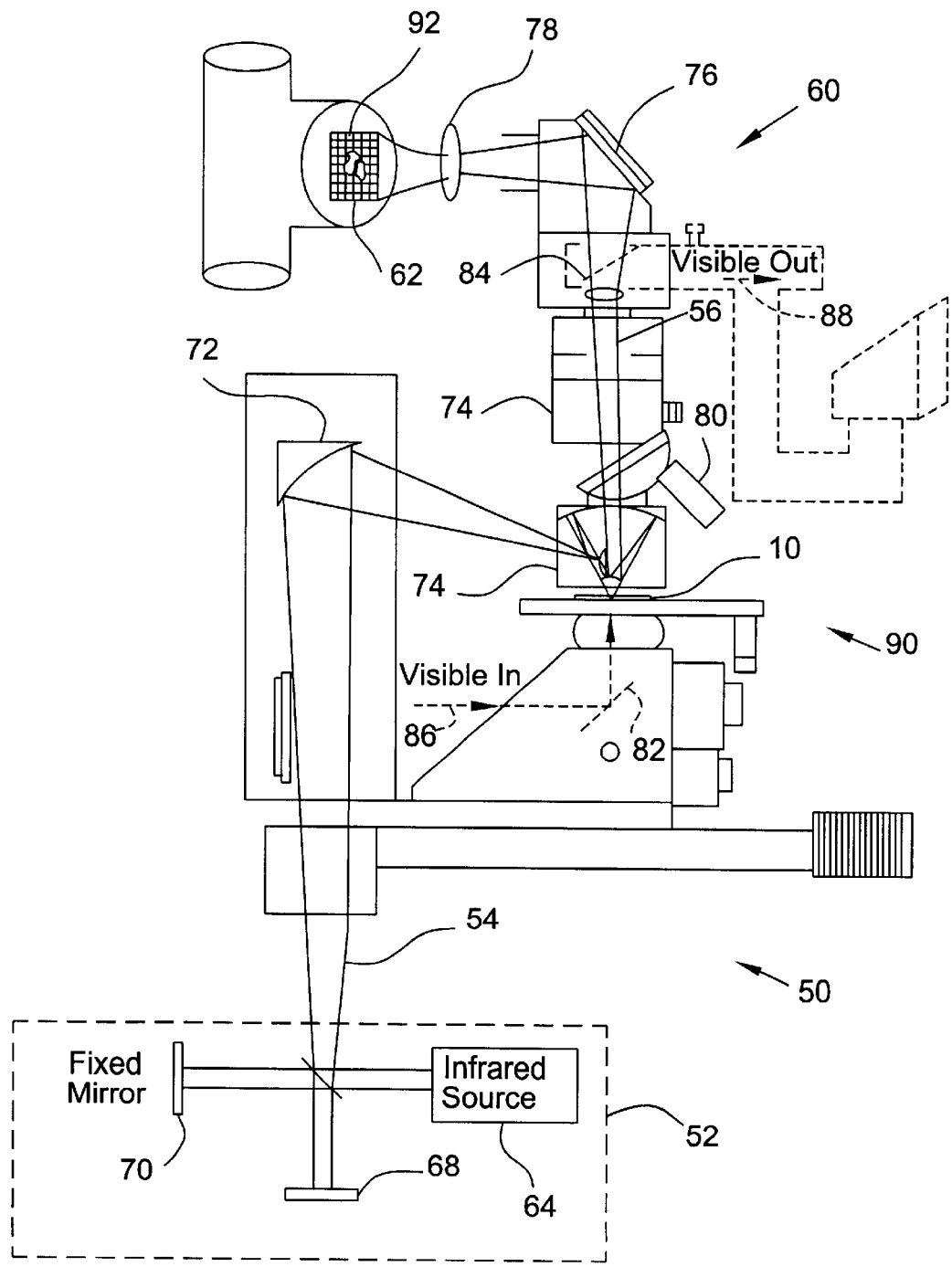
FIG. 3 is a schematic diagram showing a Fourier Transform Infrared (FT-IR) microspectroscopic imaging system for studying a biological sample according to the invention.

An embodiment of an apparatus for performing the FT-IR imaging microspectroscopy technique on the biological sample is shown in FIG. 3. The FT-IR imaging apparatus 50 includes a step-scanning FT-IR spectrometer 52 for generating infrared light 54 for illuminating the sample. The infrared light 56 reflected by the substrate and through the biological sample is collected by an FT-IR microscope 60 equipped with a focal-plane array detector 62. A suitable FT-IR spectrometer is available from the Spectroscopy Division of Bio-Rad Laboratories, Inc. of Cambridge, Massachusetts as Model FTS-60A. A suitable FT-IR microscope is also available from Bio-Rad Laboratories, Inc. as Model UMA 300A. In the illustrated embodiment, the focal-plane array detector 62 uses a mercury-cadmium-telluride (MCT) infrared detector chip with 64×64 pixels, available from Raytheon Santa Barbara Research Center. The detector is packaged in a liquid-nitrogen dewar with a four-position cold filter wheel and data acquisition electronics and software by Lockheed Martin Santa Barbara Focalplane.

In the illustrated embodiment, the FT-IR spectrometer 52 is a step-scan interferometer that includes a collimated glowbar infrared source 64. The infrared output of the source is partially reflected by a 50/50 beam splitter 66 to a movable step-scan mirror 68 and partially transmitted to a fixed mirror 70. The reflected beam from the movable mirror and the reflected beam from the fixed mirror are partially combined by the beam splitter 66 to form the output beam 54 of the spectrometer 52. The spectrometer output beam 54 is reflected by a mirror 72 to a Cassegrainian mirror 74, which focuses the infrared light to the sample 10. The infrared light reflected by the substrate of the sample (and through the sample) is collected by the Cassegrainian mirror 74 and projected by a mirror 76 to a ZnSe lens 78, which images the infrared light from the sample onto the focal-plane array detector 62.

In the illustrated embodiment of FIG. 3, the microscope includes an objective 80 for visual examination of the sample 10. To view the sample, the objective 80 is rotated into an operating position (which is the position occupied by the Cassegrainian mirror as shown in FIG. 3). Two mirrors 82 and 84 are also placed into their respective operation locations shown in FIG. 3. Visible input light 86 from the side is reflected by the mirror 82 through the substrate into the sample 10. Visible light transmitted through or scattered by the sample is collected by the objective 80 and reflected by the mirror 84 to the side. The output visible light 88 can be viewed by the user for identifying an area of interest on the biological sample or collected to form a visible image (e.g., by means of a camera) that can be compared to the infrared images of the sample. The substrate carrying the sample is mounted on a stage 90, which can be moved to position an area of interest on the sample in place for FT-IR imaging.

Figure 4:
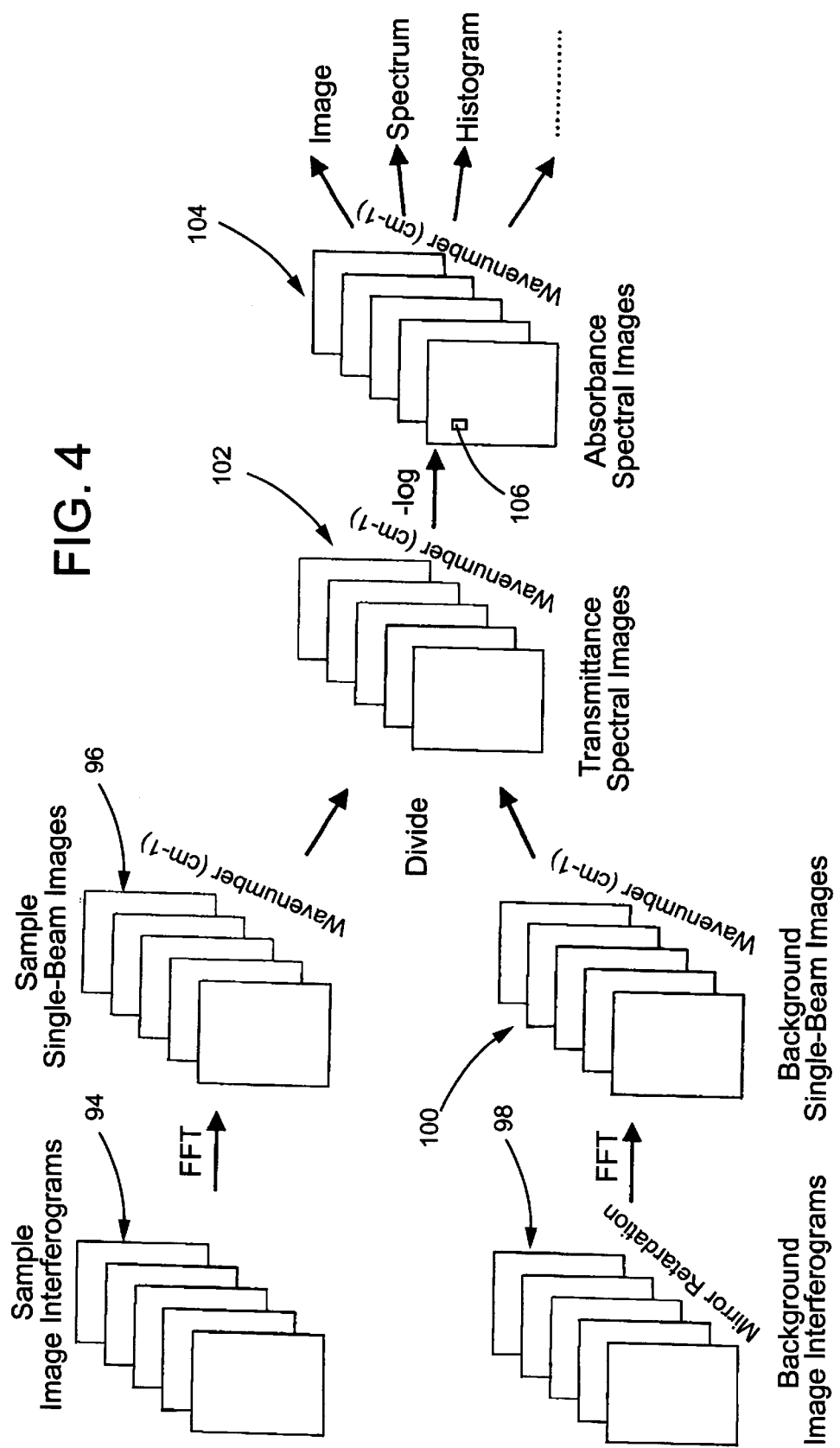
FIG. 4 is a schematic diagram showing data collection and processing of the FT-IR imaging microspectroscopy technique.

During each FT-IR image acquisition process, the movable mirror 68 of the spectrometer 52 is step-scanned at pre-selected intervals. An infrared image of the sample 10 is taken at each scan step by measuring the infrared intensity detected by each pixel 92 in the array detector 62. Referring now to FIG. 4, the images 94 of the sample taken at different scan steps, which are referred to as image interferograms, are processed by Fast Fourier Transformation (FFT) to generate a set of single-beam images 96, each corresponding to a wavenumber of infrared light.

To provide flat-field correction of the detected infrared signals, the same step-scan data acquisition is applied to a section of the substrate not covered by the biological sample to produce a set of background image interferograms 98 and the corresponding background single-beam images 100. The single-beam images 96 of the sample are numerically divided by the corresponding background single-beam images 100 to produce a set of transmittance spectral images 102. The transmittance images 102 are then processed (through a logarithmic function) to produce a set of absorbance spectral images 104 corresponding to different wavenumbers of infrared light. Each absorbance spectral image is the spectral intensity of the sample at the wavenumber of that image. For each given pixel 92 of the detector, there is a corresponding pixel 106 in each absorbance spectral image, and its spectral intensity values in the spectral images collectively form an absorbance spectrum of the sample portion imaged by that pixel. The infrared spectra of the pixels can be used to identify the cell types or existence of anomalies by, for example, comparing them to a database either by visual inspection or automatic pattern recognition techniques.

The method and system of the invention can be advantageously used to study different types of biological samples. Samples may include, but are not limited to, tissue specimens taken from a variety of organs, such as breast, prostate, bladder, colon, cervix, skin, etc. Samples may also comprise exfoliated cells supported on the substrate with the specified optical properties. A sample comprising exfoliated cells may be, for example, a Papanicolau smear, a cervical specimen, an endocervical specimen, an ectocervical specimen, a vaginal specimen, or a uterus specimen, etc. Samples may also comprise blood cells.

Significantly, the preparation of a biological sample for both the FT-IR imaging microspectroscopy and conventional pathological examination is very simple. The sample is mounted on a substrate having the optical properties described above in the same way pathological samples are mounted on conventional glass slides. The subsequent preparation of the sample for FT-IR imaging is minimal. If the sample is initially covered with paraffin, a standard deparaffinization procedure is performed before the sample is studied with the FT-IR imaging technique. The deparaffinized tissue sample is preferably stained with a suitable dye, such as Haematoxylin-Eosin (H&E), to allow easy visual identification of different cell structures under a microscope. The staining, however, is not necessary for the FT-IR imaging.

Figure 5:
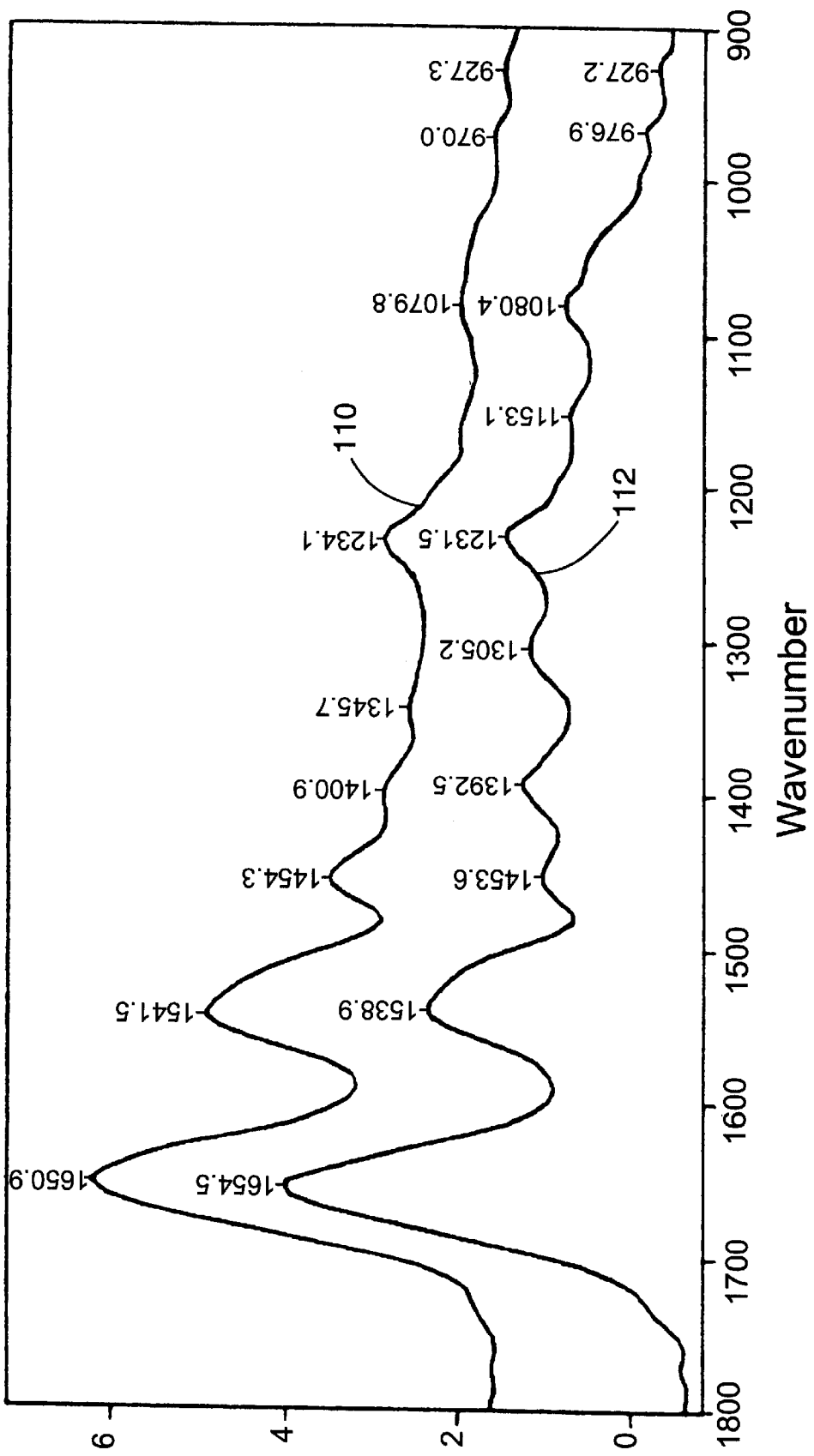
FIG. 5 shows exemplary infrared spectra of malignant human breast tissue taken with the system of FIG. 3.

The method of the invention is useful for diagnosing and monitoring disease states for biological samples, and is particularly useful for detecting and monitoring cancerous conditions in such samples. As described above, for each FT-IR microspectroscopic imaging measurement, an infrared spectrum is generated for each pixel of the focal point array detector. This infrared spectrum can be used to determine the characteristics of the portion of the sample imaged by the pixel, i.e., the sample portion from which the infrared light is detected by the pixel. By way of example, FIG. 5 shows two infrared spectra 110 and 112 taken from a sample of human breast tissue using the FT-IR imaging technique. In accordance with the invention, the sample is fixed on a substrate with a supporting surface that generally reflects infrared light and transmits visible light. Such a substrate is available from Kevley Technologies, Inc. as MirrIR low e-Glass microscope slides. The spectra shown in FIG. 5 are from a sample portion that has been visually identified as being malignant. The optical components of the FT-IR microscope used to collect images of the sample are such that each pixel in the array detector corresponds to a 12 microns by 12 microns square, roughly the size of a cell. The spectrum 110 in FIG. 5 corresponds to an area of the sample identified as connective tissue, and the spectrum 112 corresponds to an area identified as epithelial cells. The combination of visible light microscopy and infrared spectroscopic imaging data on the same tissue sample allows a direct correlation between the spectral features and observed structures.

It can be appreciated from the foregoing detailed description that the invention provides a method and system for studying biological samples that allows the same biological sample to be studied with the FT-IR imaging microspectroscopy technique and conventional pathological studies. This is achieved by fixing the biological sample on a substrate with a supporting surface that is generally transparent to visible light and generally reflective to infrared light. This type of substrate is easily available and significantly less expensive than infrared-transmitting windows commonly used in infrared transmission studies. Thus, the invention provides an alternative to the conventional way of preparing biological samples for pathological studies while providing the significant advantage of allowing the same sample to be studied with the FT-IR imaging microspectroscopy technique.

What is claimed is:

1. A method of examining biological samples comprising the steps of:

positioning a biological sample supported on a supporting surface at an imaging position, the supporting surface generally reflecting infrared light while generally transmitting visible light;

directing an infrared beam in the mid-infrared range to the biological sample;

collecting infrared images of the biological sample in a reflection-absorption mode by detecting infrared light reflected by the supporting surface and through the biological sample with a detector array having multiple detection pixels; and deriving a Fourier transform infrared (FT-IR) spectrum from the collected infrared images.

2. A method as in claim 1, wherein the supporting surface includes a coating that is generally reflective of infrared light while generally transmitting visible light.

3. A method as in claim 1, further including visually selecting a portion of interest of the biological sample and positioning the selected portion for collecting infrared images thereof.

4. A method as in claim 1, wherein the biological sample includes cellular types that are cancerous.

5. A method as in claim 1, wherein the biological sample is a tissue sample.

6. A method as in claim 5, wherein the tissue sample is stained.

7. A method as in claim 1, wherein the biological sample is a blood sample.

8. A method as in claim 1, wherein the sample includes exfoliated cells.

9. A method as in claim 1, wherein the biological sample is selected from the group of a Papanicolau smear, a cervical specimen, an ectocervical specimen, an endocervical specimen, a vaginal specimen, and a uterus specimen.

10. A method of identifying cellular types in biological samples comprising the step of:
    positioning a biological sample supported on a supporting surface at an imaging position, the supporting surface being generally reflective of infrared light while generally transmitting visible light;
    inspecting the biological sample using visible light to identify a site of interest in the sample;
    positioning the site of interest for infrared imaging with a Fourier transform infrared (FT-IR) imaging device, the FT-IR imaging device including an array detector having multiple detection pixels;
    collecting infrared images of the site of interest in a reflection-absorption mode by directing an infrared beam in the mid-infrared range to the site of interest and detecting infrared light reflected by the supporting surface and through the biological sample from the site of interest; and
    deriving an infrared spectrum from the collected infrared images for identifying cellular types at the site of interest.

11. A method as in claim 10, wherein the supporting surface includes a coatng that generally transmits visible light and generally reflects infrared light.

12. A method as in claim 10, wherein the cellular types are cancerous cells.

13. A method as in claim 10, wherein the inspecting step includes identifying cellular types at the site of interest based on visual appearance of the site of interest.

14. A method as in claim 10, wherein the biological sample is a tissue siaple.

15. A method as in claim 10, wherein the tissue sample is stained.

16. A method as in claim 10, wherein the biological sample includes exfoliated cells.

17. A method as in claim 10, wherein the biological sample is selected the group of a Papanicolau smear, a cervical specimen, an ectocervical specimen, an endocervical specimen, a vaginal specimen, and a uterus specimen.

18. A system for studying biological samples comprising:
    a biological sample supported on a supporting surface generally reflecting infrared light and generally transmitting visible light;
    a Fourier transform infrared (FT-IR) spectrometer for generating an input infrared beam in the mid-infrared range for illuminating the biological sample;
    a focal-plane array detector having multiple detection pixels for detecting infrared images of the biological sample for derivation of spectral images of the sample; and
    infrared optical elements for imaging the sample in a reflection-absorption mode wherein the infrared optical elements focuses infrared light reflected by the supporting surface and through the biological sample to the focal-plane array detector.

19. A system as in claim 18, further including optical elements for visually inspecting the biological sample for identifying a site of interest and a stage for positioning the site of interest for infrared image detection by the focal-plane array detector.

20. A system as in claim 18, wherein the supporting surface includes a coating that generally transmits visible light and generally reflects infrared light.

21. A method of examining biological samples comprising the steps of:
    positioning a biological sample supported on a supporting surface at an imaging position, the supporting surface generally reflecting infrared light;
    directing an infrared beam in the mid-infrared range to the biological sample;
    collecting infrared images of the biological sample in a reflection-absorption mode by detecting infrared light reflected by the supporting surface and through the biological sample with a detector array having multiple detection pixels; and
    deriving a Fourier transform infrared (FT-IR) spectrum from the collected infrared images.

22. A method as in claim 21, wherein the supporting surface includes a coating that is generally reflective of infrared light while generally transmitting visible light.

23. A method as in claim 22, further including visually selecting a portion of interest of the biological sample and positioning the selected portion for collecting infrared images thereof.

24. A method as in claim 21, wherein the biological sample includes cellular types that are cancerous.

25. A method as in claim 21, wherein the biological sample is a tissue sample.

26. A method as in claim 25, wherein the tissue sample is stained.

27. A method as in claim 21, wherein the biological sample is a blood sample.

28. A method as in claim 21, wherein the sample includes exfoliated cells.

29. A method as in claim 21, wherein the biological sample is selected from the group of a Papanicolau smear, a cervical specimen, an ectocervical specimen, an endocervical specimen, a vaginal specimen, and a uterus specimen.

\* \* \* \* \*